United States Patent [19]

Ozawa

[11] 4,170,900
[45] Oct. 16, 1979

[54] ROTARY SAMPLER FOR PARTICULATE MATTER

[76] Inventor: Kenneth Y. Ozawa, 760 I. St. SW., Quincy, Wash. 98848

[21] Appl. No.: 870,945

[22] Filed: Jan. 20, 1978

[51] Int. Cl.² ............................................. G01N 1/20
[52] U.S. Cl. ................................................... 73/424
[58] Field of Search ............................ 73/424, 421 A

[56] References Cited

U.S. PATENT DOCUMENTS

| | | | |
|---|---|---|---|
| 608,834 | 8/1898 | Byrnes | 73/424 |
| 621,771 | 3/1899 | Snyder | 73/424 |

FOREIGN PATENT DOCUMENTS 189607 12/1922 United Kingdom ...................... 73/424

Primary Examiner—S. Clement Swisher
Attorney, Agent, or Firm—Francis Swanson

[57] ABSTRACT

A rotary sampler for taking quality control samples from a falling stream of material is disclosed. The sampler includes an impeller which is driven by the falling material. As the impeller turns a hollow collector blade moves through the falling stream. Material within the stream is diverted through the hollow collector blade to a central collector tube. The device includes means for controlling the frequency of sampling.

8 Claims, 3 Drawing Figures

U.S. Patent　　Oct. 16, 1979　　4,170,900
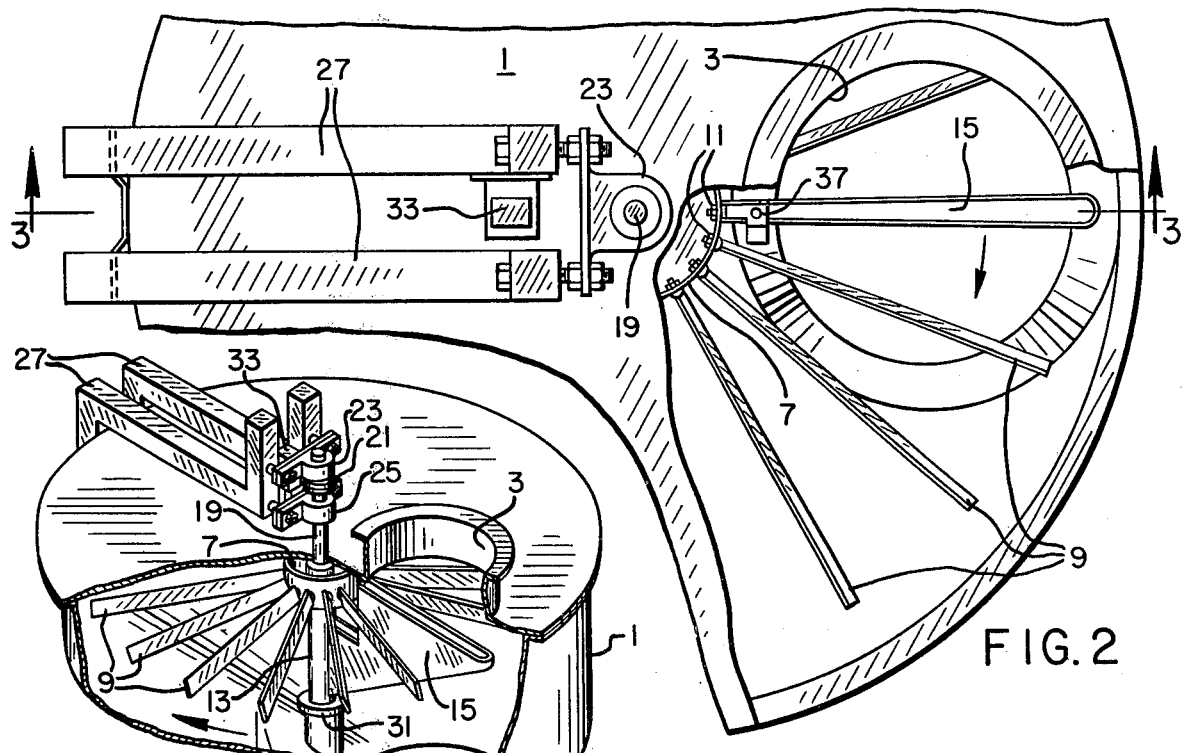
FIG.1
FIG.2
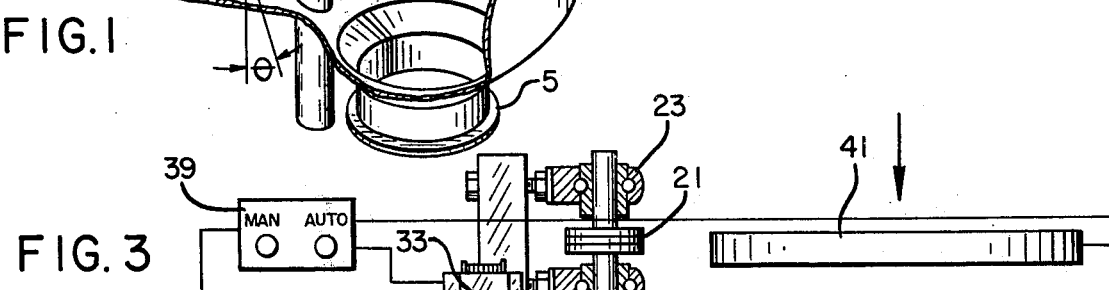
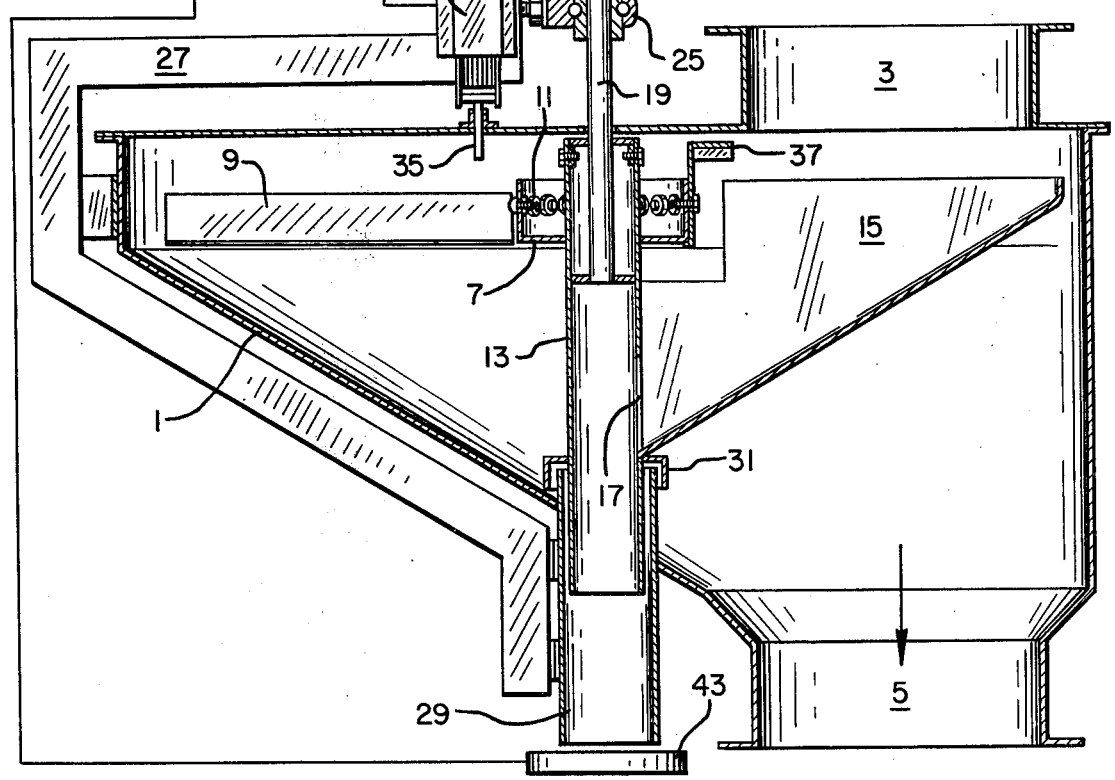
FIG.3

ROTARY SAMPLER FOR PARTICULATE MATTER

BACKGROUND OF THE INVENTION

1. Field of the Invention

The invention pertains to quality control sampling devices generally and more particularly to rotary samplers which include impellers driven by the material to be sampled.

2. Description of the Prior Art

Rotary samplers are known in the prior art. One example is disclosed in U.S. Pat. No. 3,690,179 to Olson. Closely related devices exist in the feed, seed and grain industry and are known as grain tollers. Some examples are disclosed in the following U.S. Pat. Nos. 87,176 to Klinkerman, 198,059 to Vitt and 214,734 to Waugh. While all these references disclose means for taking portions or samples of a large mass of materials, none disclose a sample taking impeller driven by the material to be sampled.

SUMMARY OF THE INVENTION

The invention provides a rotary sampler which may be used with liquids, slurrys or particulate material, or for any matter taking the form of a falling stream. The illustrated embodiment is for sampling of seeds and grains.

A principal object of the invention is to provide a device for taking accurate samples of material from a falling stream.

A further object of the invention is to provide a sampler having a rotary impeller driven by the force of the stream of material to be sampled.

A further object is to provide a sampler which may be adjusted to sample with references to the volume or weight of the material or the velocity of the material stream.

A further object of the invention is to provide a sampler which will sample at pre set time intervals or will respond to a combination of changing parameters.

Other objects and advantages will be apparent to those skilled in the art with reference to the accompanying drawings and specifications.

BRIEF DESCRIPTION OF THE DRAWINGS

FIG. 1 is a perspective view of the invention partially broken away to show the details of internal construction.

FIG. 2 is a plan view of the device partially broken away to show the relation of the impeller blades and the collector blade.

FIG. 3 is a sectional view taken along line 3—3 of FIG. 2.

DETAILED DESCRIPTION

Referring now to the drawing, FIG. 1 discloses a body (1) having a materials entry port (3) and an exit port (5). Written body (1) is an impeller (7) having blades (9) which are angularly adjustable and attached with nuts (11). The impeller (7) defines a hollow sample collector tube (13) upon which is mounted a hollow upward opening collector chute (15) which communicates with the inside of tube (13) via opening (17).

Impeller (7) and sample collector tube (13) which carries collector chute (15) rotates on shaft (19), which includes an adjustable shaft brake (21). Shaft (19) is supported by bearings (23) and (25) which are mounted on the frame (27).

A fixed sample exit tube (29) is attached to the lower end of frame (27) and to housing (1). The exit tube (29) is designed to receive and surround collector tube (13) at its lower end and direct the sample into a suitable receptical (not shown).

A collar (31) is mounted on tube (13) and surrounds the upper end of exit tube (29) to protect against entry of extraneous material from within housing (1).

The apparatus includes control means for regulating the frequency of sample taking. These means are described as follows: Mounted on frame (27) is a control solenoid (33) having a moving member (35) which intrudes into housing (1) and contacts a stop (37) mounted on impeller (7). A control circuit includes control (39) having a manual and an automatic mode and sensors (41) and (43) is shown schematically.

OPERATION

A stream of falling matter enters the port (3) and impinges on impeller blades (9) within housing (1). The stream then exits through port (5). When it is desired to take a sample, the solenoid (33) is energized, retracting member (35) out of contact with stop (37).

The falling stream impinging on blades (9) immediately causes the impeller (7) to rotate. This action moves the hollow collector chute (15) progressively through the falling stream of matter entering through port (3) and collect a sample thereof. The sample from the stream will enter the hollow chute (15) and move through opening (17) into the inside of collector tube (13) where it is directed into sample exit tube (29) and on to the sample receptical (not shown). After the collector chute (15) passes completely through the falling stream of material, the solenoid (33) is de-energized and moving member (35) moves down into the path of stop (37) so that further rotation of impeller (7) is prevented.

If control (39) is set for a pre-determined time interval the above described cycle will be repeated at the selected intervals. Alternately this cycle can be initiated through activation of the manual mode of control (39). Sensor (41) is intended to represent means for sensing the rate of flow into housing (1). Sensor (43) is intended to represent a device for sensing the weight of the sample or alternately the volume. Using sensors (41) and (43) alone or in combination and with other sensors control (39) can energize solenoid (35) in a variety of ways to initiate rotation of impeller (7) for sample collections.

As can be seen from FIGS. 1 and 2 blades (9) are mounted at an angle relative to the longitudinal axis of shaft (19). This angle can be varied by loosening nuts (11), readjusting blades (9) and retightning nuts (11). The speed of rotation can be varied by varying the number of blades as well. Shaft brake 21 can also be adjusted to control the speed of rotation.

It will be readily apparent to those skilled in this art that, with little change, this invention will work equally with liquids, slurrys or particulate matter. It will also be apparent that the sampler will function and take sampler entirely without housing (1). All that is necessary is that the impeller (7) with chute (15) move progressively through the moving stream of matter to be sampled. Furthermore, with little or no modification the apparatus could be used simply to continuously separate a distinct portion of material from a greater stream. Through adjustment of this angle and number of blades and collector chutes on the impeller, the device could be made to accurately separate out a fixed percentage of the main stream of material. Therefore, many modifications and changes can be made without departing from the true spirit and scope of the invention. I claim as my invention all such modifications and changes as fall within the scope and equivalence of the appended claims.

I claim:

1. Apparatus for sampling a moving stream of material including a body defining a material intake and exit port, a movable sample taking chute, which includes a hollow collector tube and means for controlling the frequency of sample taking means wherein the improvement comprises an impeller including a plurality of angular blades and further including at least one hollow blade which defines a sample taking chute;

the impeller response to impingement of the moving stream on the angular blades to move the chute through an entire cross-section of the moving stream;

the chute defining a hollow passage to direct material entering the chute into the hollow collector tube.

2. Apparatus for taking a sample of a stream of moving material comprising:

a frame;

an impeller on the frame comprising a plurality of angular blades mounted in spaced apart relation and including a sample taking blade which defines a sample collecting chute, the sample taking blade movable by impingement of the stream on the angular blades;

and means for controlling the frequency of sample taking.

3. Apparatus for sampling a stream of moving material comprising:

a frame;

a hollow body on the frame;

an impeller within the body;

the impeller comprising a plurality of blades mounted angular to the direction of the moving material stream, the blades set in spaced apart relation to define a plurality of spaces through which the moving stream passes;

the impeller including a sample collecting blade movable through substantially an entire cross-section of the moving stream under the influence of the stream impinging on the angular blades;

and sample taking cycle control means operatively connected to the impeller.

4. Apparatus for sampling a stream of moving material comprising:

a hollow body having material intake and exit ports;

an impeller within the body defining a sample collector tube at one end of said impeller;

angular blades on the impeller mounted so as to define a plurality of spaces through which the moving stream passes;

a hollow chute operatively attached to the collector tube, the chute movable through substantially an entire cross-section of the stream by impingement of the stream on the angular blades;

and a sampling frequency control operatively connected to the impeller.

5. Apparatus according to claim 2 wherein the frequency controlling means includes optionally disengagable means for impeding movement of the impeller.

6. Apparatus according to claim 5 wherein the optionally engagable means includes an impeller engaging solenoid operatively connected to frequency timing means.

7. Apparatus according to claim 6 wherein the frequency timing means includes means for sensing material flow rate into the body.

8. Apparatus according to claim 6 wherein the frequency timing means includes means for sensing varying material volume.

* * * * *